US 8,017,130 B2

(12) United States Patent
Nabel et al.

(10) Patent No.: US 8,017,130 B2
(45) Date of Patent: *Sep. 13, 2011

(54) METHOD OF ACCELERATED VACCINATION AGAINST EBOLA VIRUSES

(75) Inventors: Gary J. Nabel, Washington, DC (US); Nancy J. Sullivan, Kensington, MD (US); Thomas W. Geisbert, Harpers Ferry, WV (US); Peter B. Jahrling, Middletown, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/613,018

(22) Filed: Nov. 5, 2009

(65) Prior Publication Data

US 2010/0047282 A1    Feb. 25, 2010

Related U.S. Application Data

(63) Continuation of application No. 11/332,976, filed on Jan. 17, 2006, now Pat. No. 7,635,485, which is a continuation of application No. PCT/US2004/024781, filed on Aug. 2, 2004.

(60) Provisional application No. 60/491,933, filed on Aug. 1, 2003.

(51) Int. Cl.
*A61K 39/12*    (2006.01)
*A61K 39/23*    (2006.01)
*A61K 39/275*    (2006.01)

(52) U.S. Cl. ............... 424/199.1; 424/204.1; 424/233.1
(58) Field of Classification Search .................. None
See application file for complete search history.

(56) References Cited

U.S. PATENT DOCUMENTS

| 6,544,780 B1 | 4/2003 | Wang |
| 6,756,523 B1 | 6/2004 | Kahn et al. |
| 6,964,762 B2 | 11/2005 | Wang et al. |

FOREIGN PATENT DOCUMENTS

| WO | WO 03/028632 A | 4/2003 |
| WO | WO 03/038057 A | 5/2003 |
| WO | WO 03/070920 A | 8/2003 |
| WO | WO 03/092582 A | 11/2003 |

OTHER PUBLICATIONS

Center for Biosecurity, University of Pittsburgh Medical Center, Hemorragic Fever Viruses (VHF), 2008, (www.upmc-biosecurity.org).
Sullivan et al., Immune Protection of Nonhuman Primates Against Ebola Virus with Single Low-Dose Adenovirus Vectors Encoding Modified GPs, 2006, PLoS Medicine, vol. 3, 6 pages 865-873.
Cohen, Immunity's yin and yang a Successful Vaccine Must First Avoid Being Eliminated by Preexisting Immunity Before it can Promote a Protective Immune Response, IAVI report, downloaded from http://www.iavireport.org/issues/issue10-1/immunity.asp on Jun. 2, 2008.
Varnavski et al., Preexisting Immunity to Adenovirus in Rhesus Monkeys Fails to Prevent Vector-Induced Toxicity, 2002, Journal of Virology, vol. 76, No. 11, pp. 5711-5719.
Warfield et al., Ebola virus-like particle-based vaccine protects nonhuman primates against lethal Ebola virus challenge, 2007, Journal of Infectious Diseases, vol. 196, Supplemental 2, pp. S430-437.
Goodchild, Vaccine for Ebola virus, 2008, EurekAlert, downloaded from http://www.eurekalert.org/pub_releases/2008-03/sfgmvfe032808.php on Jun. 2, 2008.
Chen P., et al., "Effective repeat administration with adenovirus vectors to the muscle", Gene Therapy (2000) vol. 7, pp. 587-595.
Farina S. F., et al., "Replication-Defective Vector Based on a Chimpanzee Adenovirus", Journal of Virology, Dec. 2001, vol. 75, No. 23, pp. 11603-11613.
Havenga, M. J. E., et al., "Improved Adenovirus Vectors for Infection of Cardiovascular Tissues", Journal of Virology, Apr. 2001, vol. 75, No. 7, pp. 3335-3342.
Havenga, M. J. E., et al., "Exploiting the Natural Diversity in Adenovirus Tropism for Therapy and Prevention of Disease", Journal of Virology, May 2002, vol. 76, No. 9, pp. 4612-4620.
Kass-Eisler, A., et al., "Circumventing the immune response to adenovirus mediated gene therapy", Gene Therapy (1996), vol. 3, pp. 154-162.
Mastrangeli, A., et al., "Sero-Switch Adenovirus-Mediated In Vivo Gene Transfer: Circumvention of Anti-Adenovirus Humoral Immune Defenses Against Repeat Adenovirus Vector Administration by ChanQinQ the Adenovirus Serotype", Human Gene Therapy, Jan. 1, 1996, vol. 7, pp. 79-87.
Vogels R., et al., "Replication-Deficient Human Adenovirus Type 35 Vectors for Gene Transfer and Vaccination: Efficient Human Cell Infection and Bypass of Preexisting Adenovirus Immunity", Journal of Virology, Aug. 2003, vol. 77, No. 15, pp. 8263-8271.
Aoki, K. et al. 1999 "Efficient generation of recombinant adenoviral vectors by ere-lox recombination in vitro." Mol. Med. 5:224-231.
Chan, S.Y. et al. 2000 "Differential induction of cellular detachment by envelope Iglycoproteins of Marburg and Ebola (Zaire) viruses." J. Gen Virol.81:2155-2159.
Feldmann, H. et al. 2003 "Ebola virus: from discovery to vaccine." Nature Rev. 3:677-685.
Gupta, M. et al. 2001 "Passive transfer of antibodies protects immunocompetent and immunodeficient mice against lethal Ebola virus infection without complete inhibition of viral replication." J. Virol. 75:4649-4654.
Hart, M.K. 2003 "Vaccine research efforts for filoviruses." Int. J. Parasitol. 33:583-595.
Hevey, M. et al. 1998 "Marburg virus vaccines based upon Alphavirus replicons protect Iguinea pigs and non-human primates." ViroloJ!Y 251 :28-37.

(Continued)

*Primary Examiner* — Mary E Mosher
*Assistant Examiner* — Benjamin P Blumel
(74) *Attorney, Agent, or Firm* — Kilpatrick Townsend and Stockton LLP

(57) ABSTRACT

The present invention relates to genetic vaccines for stimulating cellular and humoral immune responses in humans and other hosts, and, in particular, relates to recombinant viruses that express heterologous antigens of pathogenic viruses, in single dose form.

9 Claims, 7 Drawing Sheets

OTHER PUBLICATIONS

Jahrling, P.B. et al. 1996 "Passive immunization of Ebola virus-infected cynomolgus monkeys with immunoglobulin from hyperimmune horses." Arch. Virol. Suppl. 11: 135-140.

Jahrling, P.B. et al. 1999 "Evaluation of immune globulin and recombinant interferon-a2b for treatment of experimental Ebola virus infections." J. Infect. Dis. 179:5224-5234.

Ksiazek, T.G. et al. 1992 "Enzyme immunosorbent assay for Ebola virus antigens in tissues of infected primates." J. CUn. Microbiol. 30:947-950.

Ohno, T. et al. 1994 "Gene therapy for vascular smooth muscle cell proliferation after arterial injury." Science 265: 781-784.

Parren, P.W.I. et al. 2002 "Pre- and postexposure prophylaxis of Ebola virus infection in an animal model by passive transfer of a neutralizing human antibody." J. Virol. 76:6408-6412.

Sanchez, A. et al. 1998 "Biochemical analysis of the secreted and virion glycoproteins of Ebola virus." J. Virol. 72:6442-6447.

Sullivan, N.J. et al. 2000 "Development of a preventive vaccine for Ebola virus infection in primates." Nature 408:605-609.

Sullivan, N.J. et al. 2003 "Accelerated vaccination for Ebola virus haemorrhagic fever in non-human primates." Nature 424:681-684.

Takada, A. et al. 2000 "Downregulation of 131 integrins by Ebola virus glycoprotein: implication for virus entry." Virology 278:20-26.

Tang, M. et al. 2002 "Recombinant adenovirus encoding the HA gene from swine H3N2 influenza virus partially protects mice from challenge with heterologous virus: A/HK/1/68 (H3N2)." Arch. Virol. 147:2125-2141.

Tatsis, N. et al. 2004 "Adenoviruses as vaccine vectors." Mol. Ther. 10:616-629.

Volchkov, V.E. et al. 2001 "Recovery of infectious Ebola virus from complementary DNA: RNA editing of the GP gene and viral cytotoxicity." Science 291: 1965-1969.

Walsh, P.D. et al. 2003 "Catastrophic ape decline in western equatorial Africa." Nature 422:611-614.

Wesseling, J.G et al. 1993 "Mouse hepatitis virus spike and nucleocapsid proteins expressed by adenovirus vectors protect mice against a lethal infection." J. Gen. Virol. 74:2061-2069.

Wilson, J.A. & Hart, M.K. 2001 "Protection from Ebola virus mediated by cytotoxic T lymphocytes specific for the viral nucleoprotein." J. Virol. 75:2660-2664.

Xiang, Z.Q. et al. 1996 "A replication-defective human adenovirus recombinant serves as a highly efficacious vaccine carrier." ViroloRY 219:220-227.

Xu, L. et a1.1998 "Immunization for Ebola virus infection." Nature Med. 4:37-42.

Yang, Z.-Y. et al. 2000 "Identification of the Ebola virus glycoprotein as the main viral, determinant of vascular cell cytotoxicity and injury." Nature Med. 6:886-889.

Yang, Z-Y. et al. 2003 "Overcoming immunity to a viral vaccine by DNA priming before vector boostin,g." J. Virol. 77:799-803.

Ye, W.W. et al. 1991 "Co-expression of hepatitis B virus antigens by a non-defective adenovirus vaccine vector." Arch. Viral. 118: 11-27.

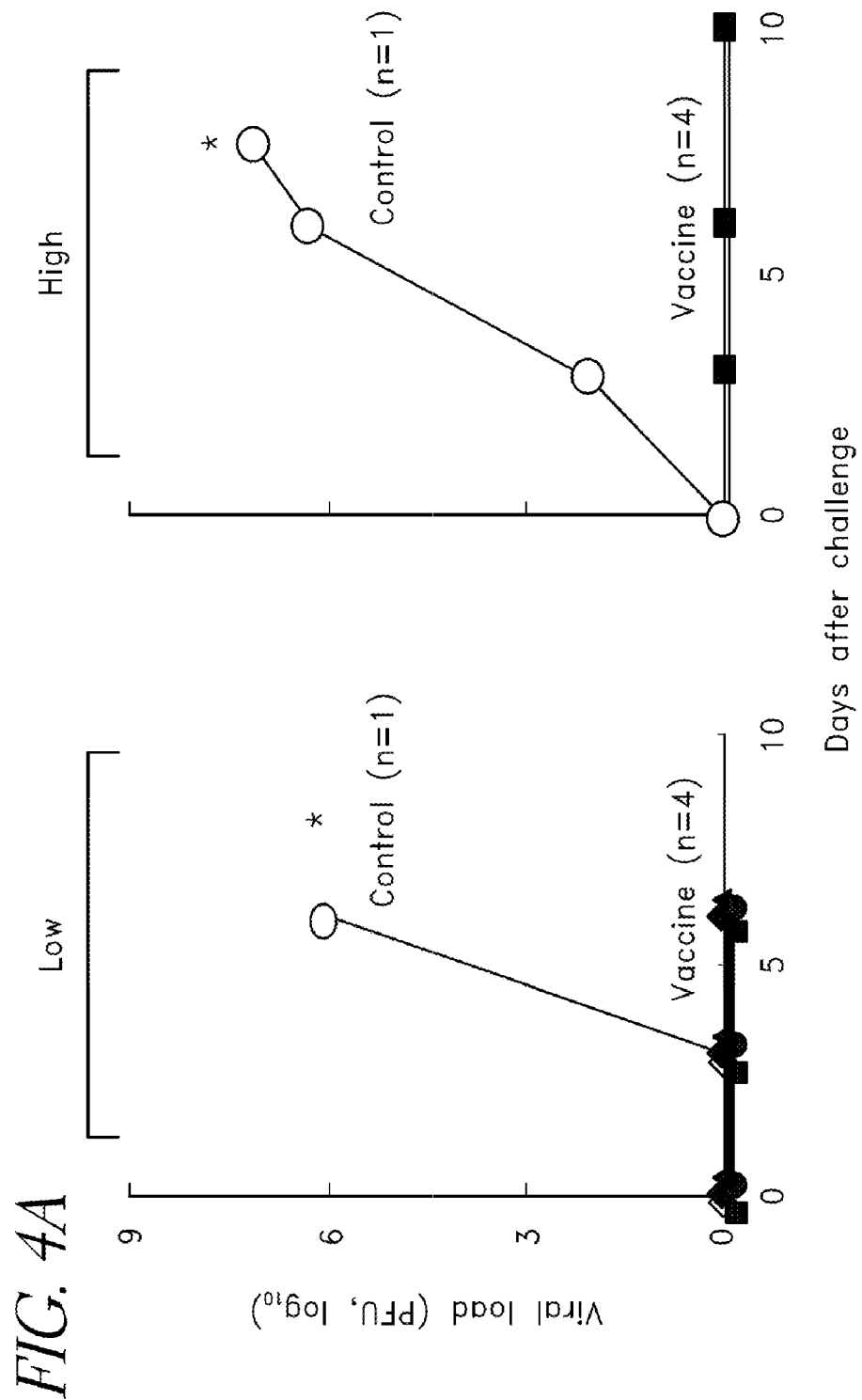

METHOD OF ACCELERATED VACCINATION AGAINST EBOLA VIRUSES

RELATED APPLICATIONS

This application is a Continuation of U.S. application Ser. No. 11/332,976, filed Jan. 17, 2006 which is a Continuation of the International Patent Application No.: PCT/US2004/024781 filed Aug. 2, 2004, designating the U.S. and published in English on Feb. 10, 2005 as WO 2005/012538, which claims the benefit of U.S. Provisional Application No. 60/491,933, filed Aug. 1, 2003, all of which are hereby incorporated by reference in their entireties.

BACKGROUND OF THE INVENTION

Ebola virus is an aggressive pathogen that causes a highly lethal hemorrhagic fever syndrome in humans and nonhuman primates. First recognized near the Ebola River valley during an outbreak in Zaire in 1976 (Bowen, E. T. et al. 1977 *Lancet* 1:571-573: Johnson, K. M. et al. 1977 *Lancet* 1:569-571), outbreaks have occurred in Africa in the ensuing 27 years, with mortality rates ranging from 50 to 90% (Peters, C. J. and Khan, A. S. 1999 *Curr Top Microbiol Immunol* 235:85-95; Sanchez, A. et al. 2001 Filoviridae: Marburg and Ebola viruses in Fields Virology, D. M. Knipe and P. M. Howley (eds.), Lippincott, Williams & Wilkins, Philadelphia, Pa., p. 1279-1304). The natural host for Ebola virus is unknown, so it has not been possible to implement programs to control or eliminate viral reservoirs of transmission to human populations. The rapid progression of Ebola virus infection has further complicated the control of this disease, affording little opportunity to develop acquired immunity. There is currently no antiviral therapy or vaccine that is effective against Ebola virus infection in humans.

SUMMARY OF THE INVENTION

In one aspect, the invention is related to a recombinant virus comprising: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus, the recombinant virus being replication competent or replication defective adenovirus or related virus; in single dose form.

In another aspect, the invention is related to a recombinant virus comprising: a plurality of antigen sequences heterologous to the recombinant virus, each encoding a viral antigen from a pathogenic virus, expression of the plurality of the antigen sequences eliciting an immune response directed against the viral antigen and cells expressing the viral antigen in the host upon infection of the host by the recombinant virus, the recombinant virus being replication competent or replication defective adenovirus or related virus; in single dose form.

In another aspect, the invention is related to a method of accelerated vaccination comprising single dose administration to a host of a recombinant virus comprising: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus, the recombinant virus being replication competent or replication defective adenovirus or related virus.

In another aspect, the invention is related to a method of accelerated vaccination comprising single dose administration to a host of a recombinant virus comprising: a plurality of antigen sequences heterologous to the recombinant virus, each encoding a viral antigen from a pathogenic virus, expression of the plurality of the antigen sequences eliciting an immune response directed against the viral antigen and cells expressing the viral antigen in the host upon infection of the host by the recombinant virus, the recombinant virus being replication competent or replication defective adenovirus or related virus.

In a related aspect, the invention is related to a pharmaceutical composition comprising a first recombinant virus comprised of an antigen sequence heterologous to the recombinant virus that encodes a first viral antigen from a pathogenic virus, expression of the viral antigen eliciting an immune response directed against the viral antigen and cells expressing the viral antigen in the host upon infection of the host by the recombinant virus, the recombinant virus being replication competent or replication defective adenovirus or related virus, and a second recombinant virus comprised of an antigen sequence heterologous to the recombinant virus that encodes a second viral antigen from the same pathogenic virus, expression of the viral antigen eliciting an immune response directed against the viral antigen and cells expressing the viral antigen in the host upon infection of the host by the recombinant virus, the recombinant virus being replication competent or replication defective adenovirus or related virus, where the first viral antigen is a surface antigen and the second viral antigen is a core antigen; in single dose form.

In another aspect, the invention is related to a pharmaceutical composition comprising a recombinant virus comprised of a plurality of antigen sequences heterologous to the recombinant virus, at least one encoding a first viral antigen from a pathogenic virus, and at least another encoding a second viral antigen from the same pathogenic virus, expression of the plurality of the antigen sequences eliciting an immune response directed against the viral antigen and cells expressing the viral antigen in the host upon infection of the host by the recombinant virus, the recombinant virus being replication competent or replication defective adenovirus or related virus, where the first viral antigen is a surface antigen and the second viral antigen is a core antigen; in single dose form.

In another aspect, the invention is related to a method of accelerated vaccination comprising single dose administration to a host of a pharmaceutical composition comprising a first recombinant virus comprised of an antigen sequence heterologous to the recombinant virus that encodes a first viral antigen from a pathogenic virus, expression of the viral antigen eliciting an immune response directed against the viral antigen and cells expressing the viral antigen in the host upon infection of the host by the recombinant virus, the recombinant virus being replication competent or replication defective adenovirus or related virus and a second recombinant virus comprised of an antigen sequence heterologous to the recombinant virus that encodes a second viral antigen from a pathogenic virus, expression of the viral antigen eliciting an immune response directed against the viral antigen and cells expressing the viral antigen in the host upon infection of the host by the recombinant virus, the recombinant virus being replication competent or replication defective adenovirus or related virus, where the first viral antigen is a surface antigen and the second viral antigen is a core antigen.

In another aspect, the invention is related to a method of accelerated vaccination comprising single dose administration to a host of a pharmaceutical composition comprising a recombinant virus comprised of a plurality of antigen sequences heterologous to the recombinant virus, at least one encoding a first viral antigen from a pathogenic virus, and at least another encoding a second viral antigen from the same pathogenic virus, expression of the plurality of the antigen sequences eliciting an immune response directed against the viral antigen and cells expressing the viral antigen in the host upon infection of the host by the recombinant virus, the recombinant virus being replication competent or replication defective adenovirus or related virus, where the first viral antigen is a surface antigen and the second viral antigen is a core antigen.

DETAILED DESCRIPTION OF THE PREFERRED EMBODIMENT

Figure 1A:
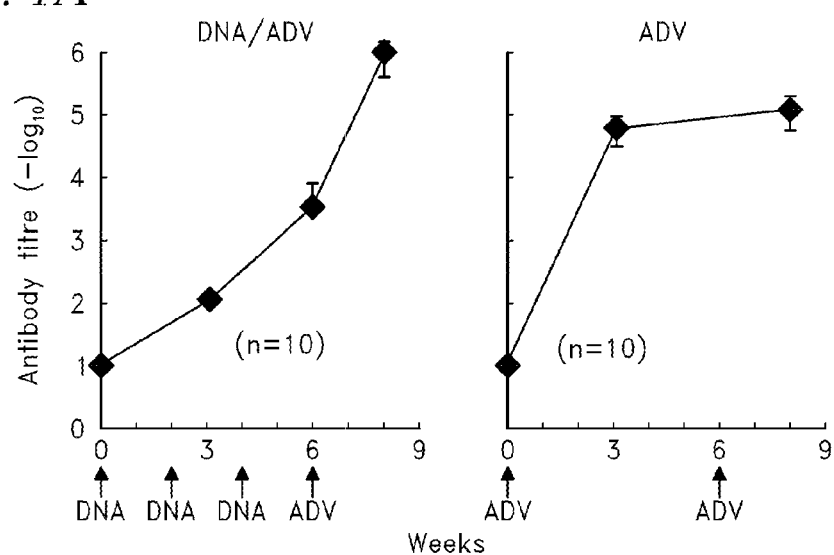
FIG. 1. Comparison of the Ebola-specific antibody responses by heterologous DNA/ADV prime-boost or ADV prime-boost vaccination in mice. a) The time course of Ebola-specific antibody responses by DNA prime and adenovirus boost compared with adenoviral immunization alone is shown (see Example 1). Data represent the relative ELISA titer to Ebola GP after immunization with DNA/ADV-GP or ADV-GP/ADV-GP in BALB/c mice using a log scale. b) Immunization schedule for previously used heterologous prime-boost vaccine (top), adenoviral prime and boost (middle), and single adenoviral virus (bottom) immunizations. Challenge was performed with a 1995 isolate of Ebola virus (Zaire) at 32, 10 or 4 weeks after the initial immunization, respectively.

Containment of highly lethal Ebola virus outbreaks poses a serious public health challenge. Although an experimental vaccine has successfully protected non-human primates against disease (Sullivan, N. J. et al. 2000 *Nature* 408:605-609), more than six months was required to complete the immunizations, making it impractical to limit an acute epidemic. Here, we report the development of accelerated vaccination against Ebola virus in non-human primates. The antibody response to immunization with an adenoviral (ADV) vector encoding the Ebola glycoprotein (GP) was induced more rapidly than with DNA priming and ADV boosting, but it was of lower magnitude. To determine whether this earlier immune response could nonetheless protect against disease, cynomolgus macaques were challenged with Ebola virus after vaccination with ADV-GP and nucleoprotein (NP) vectors. Protection was highly effective and correlated with the generation of Ebola-specific CD8+ T-cell and antibody responses. Even when animals were immunized once with ADV-GP/NP and challenged 28 days later, they remained resistant to challenge with either low or high doses of virus. This accelerated vaccine provides an intervention that is envisioned to help to limit the epidemic spread of Ebola, and is applicable to other viruses.

Genetic Vaccines of the Present Invention

The present invention relates to genetic vaccines for stimulating cellular and humoral immune responses in humans and other hosts, and, in particular, relates to recombinant viruses that express heterologous antigens of pathogenic viruses, in single dose form.

In one embodiment, a recombinant virus is provided as a viral vaccine for eliciting an immune response in a host infected by the virus. The recombinant virus comprises: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus. The recombinant virus is replication competent or replication defective (i.e., incompetent).

In a related embodiment, a pharmaceutical composition is provided comprising a first recombinant virus comprised of: an antigen sequence heterologous to the recombinant virus that encodes a first viral antigen from a pathogenic virus, expression of the viral antigen eliciting an immune response directed against the viral antigen and cells expressing the viral antigen in the host upon infection of the host by the recombinant virus, and a second recombinant virus comprising an antigen sequence heterologous to the recombinant virus that encodes a second viral antigen from the same pathogenic virus, expression of the viral antigen eliciting an immune response directed against the viral antigen and cells expressing the viral antigen in the host upon infection of the host by the recombinant virus, where the first viral antigen is a surface antigen and the second viral antigen is a core antigen.

In another embodiment, a recombinant virus is provided as a viral vaccine for eliciting an immune response against multiple antigens in a host infected by the virus. The recombinant virus comprises: a plurality of antigen sequences heterologous to the recombinant virus, each encoding a viral antigen from a pathogenic virus, expression of the plurality of the antigen sequences eliciting an immune response directed against the viral antigen and cells expressing the viral antigen in the host upon infection of the host by the recombinant virus. The recombinant virus is replication competent or replication defective (i.e., incompetent).

In a related embodiment, a pharmaceutical composition is provided comprising a recombinant virus comprised of: a plurality of antigen sequences heterologous to the recombinant virus, at least one encoding a first viral antigen from a pathogenic virus, and at least another encoding a second viral antigen from the same pathogenic virus, expression of the plurality of the antigen sequences eliciting an immune response directed against the viral antigen and cells expressing the viral antigen in the host upon infection of the host by the recombinant virus, where the first viral antigen is a surface antigen and the second viral antigen is a core antigen.

The vaccines of the present invention can be used to immunize the host against a wide variety and different strains of pathogenic viruses such as HIV-1, HIV-2, herpes simplex virus type 1, herpes simplex virus type 2, influenza virus, Marburg virus, Ebola virus, and hepatitis A, B, C, D, and E viruses.

The recombinant virus of the present invention can be used to express multiple antigen sequences simultaneously from the same viral vector. Thus, the recombinant virus may encode multiple antigens from the same strain of pathogenic virus, from different strains of the same pathogenic viruses, or from different antigens from different kind of viruses. This enables the vaccines of the present invention to be utilized to immunize against a broad-spectrum of viruses.

The present invention is directed to vaccines that mimic the features of a native pathogenic virus, but without eliciting pathogenicity, thus causing the host to mount an effective defense, while not being in any actual danger of infection. The genetic vaccines are replication competent or replication defective viruses into which one or more DNA sequences encoding one or more viral antigens are inserted into the regions of the viral genome non-essential to its infectivity. The recombinant virus expresses the viral antigens and elicits an immune response in vivo directed against the antigens and cells expressing the antigens.

In one embodiment, a recombinant virus is provided for eliciting an immune response in a host infected by the virus. The recombinant virus comprises: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus. The recombinant virus is replication competent or replication defective (i.e., incompetent).

The recombinant virus may be constructed from any virus, where the native progenitor is replication competent or is rendered replication defective. For example, adenovirus, adeno-associated virus (AAV), SV40 virus, retrovirus, herpes simplex virus or vaccinia virus may be used to generate the recombinant virus by inserting the viral antigen into the region non-essential to the infectivity of the recombinant virus. It is preferred that the recombinant virus does not have the pathologic regions of the native progenitor of the wild type virus but retains its infectivity to the host.

In one embodiment, the recombinant virus is a replication competent or replication defective adenovirus or related virus.

Adenoviruses are DNA viruses with a 36-kb genome. There are 51 human adenovirus serotypes that have been distinguished on the basis of their resistance to neutralization by antisera to other known adenovirus serotypes. Although the majority of adenoviral vectors are derived from serotypes 2 and 5, other serotypes such as type 35 may also be used. The wild type adenovirus genome is divided into early (E1 to E4) and late (L1 to E5) genes. Adenovirus vectors can be prepared to be either replication competent or non-replicating. Foreign genes can be inserted into three areas of the adenovirus genome (E1, E3, or E4) as well as behind the major late promoter. The ability of the adenovirus genome to direct production of adenoviruses is dependent on sequences in E1.

In some cases, it may be desirable to utilize a non-replicating adenovirus vector vaccine due to safety considerations. To generate non-replicating adenoviral vectors, E1A and E1B sequences may be deleted and substituted with an expression cassette that encodes antigen. The adenovirus vector with its expression cassette is E1− and thus incapable of replicating. To replicate the recombinant adenovirus, the vector DNA is transfected into a complementary cell line that contains E1 sequences within its genome. In other cases, replication competent adenovirus vectors are preferable for use as vaccines because viral replication is desired to increase the amount of immunizing epitope produced from inserted gene sequence. Because the entire adenovirus E3 region can be deleted without a major change in viral growth in tissue cultured cells, this region can be substituted with foreign DNA and the adenovirus grown in any cell line permissive for wild type adenovirus infection.

Efficient infection by adenovirus (Ad) or by a replication-defective (E1−) Ad vector of a cell or target tissue is mediated by the Ad vector proteins and their interaction with the host cell. Applying the knowledge that there are 51 immunologically distinct Ad serotypes, investigators have previously shown that repeat administration can be accomplished if two vectors based on different serotypes are used sequentially. Based on these observations, the type-determining epitopes of the Ad capsid proteins may be identified and altered by genetic engineering to generate serologically distinct Ads. These modified Ads could then be used as effective vectors in individuals with prior immunity to adenovirus, without compromising vector stability or expression of the transgene. The three major components of the capsid; fiber, hexon, and penton base, are targets of antiviral host responses, but the relative contribution of each to type determination and in vivo protection needs to be elucidated. By replacing the Ad type 5 (Ad5) hexon gene with sequences from Ad2, investigators have changed the type specificity of the chimeric virus. Construction of Ad hexon serotype chimeras is contemplated, indeed construction of sertotype chimeras of Ad hexon, penton, fiber, and epitopes and parts thereof that mediate the antiviral response, is envisioned in the circumvention of host immune responses to adenoviral infection.

Adeno-associated viruses (AAVs) are non-pathogenic, replication-defective, helper-dependent parvoviruses (or "dependoviruses", or "adeno-satellite viruses"). There are at least six recognized serotypes designated as AAV-1, AAV-2, AAV-3, AAV-4, AAV-5 AAV-X7, etc. Recombinant AAV (rAAV) virions are of interest as vectors for vaccine preparations because of their broad host range, excellent safety profile, and duration of transgene expression in infected hosts. One remarkable feature of recombinant AAV (rAAV) virions is the prolonged expression achieved after in vivo administration (Fisher et al., 1997 Nat Med 3:306-312; Flotte et al., 1993 PNAS USA 90:10613-10617; and Xiao et al., 1996 J Virol 70:8098-8108.) rAAV-antigen transduction results in entry of the antigen into the classical MHC Class I processing pathway and the formation of antigen-specific cytotoxic T lymphocytes and antibodies in vivo.

The recombinant adenovirus or related virus of the present invention can direct high levels of antigen expression that provide strong stimulation of the immune system. Adenoviruses or related viruses can be used to deliver DNA that encodes for an antigen that is useful as an immunizing agent against another infectious virus. Both the humoral and cell-mediated immune responses can be stimulated by this approach. Moreover, the recombinant adenovirus may naturally infect airway and gut epithelial cells in humans, and therefore the vaccine may be delivered through nasal spray or oral ingestion. In addition, the recombinant adenovirus of the present invention should be safe because it is replication incompetent.

The expression of the viral antigen may be controlled by a promoter homologous to the native progenitor of the recombinant virus. Alternatively, the expression of the viral antigen may be controlled by a promoter heterologous to the native progenitor of the recombinant virus. For example, the promoter heterologous to the native progenitor of the recombinant virus may be a eukaryotic promoter such as insulin promoter, human cytomegalovirus (CMV) promoter and its early promoter, simian virus SV40 promoter, Rous sarcoma virus LTR promoter/enhancer, the chicken cytoplasmic β-actin promoter, and inducible promoters such as the tetracycline-inducible promoter.

The pathogenic virus may be any pathogenic virus that causes pathogenic effects or disease in a host such as human, domestic animals or other mammals. Thus, the recombinant virus can be used as a vaccine for protecting the host from infection of the pathogenic virus. Table 1 provides a list of antigens that may be used by the present invention to elicit a cellular and humoral immune response.

TABLE 1

| Virus | Surface Antigen | Core Antigen |
|---|---|---|
| Influenza (A, B, C) | GPs (HA1, HA2, NA) | NP |
| Respiratory syncytial virus (RSV) | F and G proteins | N |
| Enteroviruses e.g., Poliovirus | VP1, VP2, VP3 | |
| Flaviviruses West Nile Virus (WNV) Dengue | M and E proteins | NS |
| Hepatitis B | SHBsAg, MHBsAg, LHBsAg | HBcAg, HBeAg |
| Hepatitis C | Envelope, NS3, NS4 | Core protein |
| Filoviruses Marburg Ebola (Zaire, Sudan, Reston, Cote d'Ivoire) | GPs (GP, sGP) | NP |

TABLE 1-continued

| Virus | Surface Antigen | Core Antigen |
|---|---|---|
| Measles | F and H proteins | N |
| Arenaviruses e.g., Lassa | GP | NP |
| Retroviruses e.g., HTLV | Gag, Env | |
| HIV | gp120 (V3 region), gp41 | Core proteins, RT |
| Papillomavirus | L1 | E1, E2, E6, E7 |
| Herpes Simplex Virus | gB, gD | ICP4 |
| Epstein Barr Virus | gp350 | Numerous lytic and latent antigens |
| Coronaviruses e.g., Severe Acute Respiratory Syndrome (SARS)-CoV | S, M, E | N, M |

In a variation, the pathogenic virus may be an influenza virus. The viral antigen may be an influenza glycoprotein such as influenza HA1, HA2 or NA, or a core protein such as nucleoprotein.

In another variation, the pathogenic virus may be a respiratory syncytial virus (RSV). For example, the RSV viral antigen may be the glycoprotein (G-protein) or the fusion protein (F-protein), or the nucleoprotein (N-protein).

In another variation, the pathogenic virus may be an enterovirus. For example, the enteroviral antigen may be VP1, VP2 or VP3.

In another variation, the pathogenic virus may be a flavivirus such as West Nile Virus or Dengue Virus. For example, the flaviviral antigen may be a membrane (M) protein or envelope (E) protein, or a nonstructural (NS) protein.

In yet another variation, the pathogenic virus may be a hepatitis virus such as hepatitis A, B, C, D or E virus. The viral antigen may be a surface antigen or core protein of hepatitis A, B, C, D or E virus. For example, the viral antigen may be a surface antigen or core protein of hepatitis B virus such as the small hepatitis B surface antigen (SHBsAg), the middle hepatitis B surface antigen (MHBsAg) or the large hepatitis B surface antigen (LHBsAg). The viral antigen may also be a surface antigen or core protein of hepatitis C virus such as envelope protein, NS3 antigen or NS4 antigen, or core protein.

In another variation, the pathogenic virus may be a filovirus such as Ebola virus or Marburg Virus. For example, the viral antigen may be an Ebola glycoprotein or surface antigen such as Ebola GP protein or sGP protein, or a core protein such as nucleoprotein (NP).

In another variation, the pathogenic virus may be measles virus and the viral antigen may be fusion protein (F) or hemagglutinin (H), or nucleoprotein (N).

In another variation, the pathogenic virus may be an arenavirus such as Lassa virus. For example, the viral antigen may be a Lassa surface antigen such as a glycoprotein (GP) or a core protein such as nucleoprotein (NP).

In another variation, the pathogenic virus may be a retrovirus such as one of various strains of human immunodeficiency virus (HIV) including HIV-1 and HIV-2. The viral antigen may be a HIV glycoprotein (or surface antigen) such as HIV GP120 and GP41, a capsid protein (or structural protein) such as HIV P24 protein, or other HIV regulatory protein such as Tat, Vif and Rev proteins, or a core protein such as RT.

In yet another variation, the viral antigen may be a surface antigen such as L1 of human papillomavirus or a core antigen like E1, E2, E6, or E7.

In yet another variation, the pathogenic virus may be a herpes simplex virus (HSV) such as HSV-1 and HSV-2. For example, the HSV viral antigen may be glycoprotein B or glycoprotein D from HSV-2, or an HSV regulatory protein such as ICP4.

In still another variation, the pathogenic virus may be an Epstein Barr Virus (EBV). For example, the EBV viral antigen may be glycoprotein 350 or one or more of numerous lytic and latent antigens.

In yet another variation, the pathogenic virus may be a coronavirus such as the SARS-Coronavirus that is associated with Severe Acute Respiratory Syndrome (SARS). For example, the viral antigen may be a surface antigen such as S, M, or E, or a core antigen such as N or M.

It is noted that other virus-associated proteins or antigens are readily available to those of skill in the art. Selection of the pathogenic virus and the viral antigen is not a limiting factor in this invention.

The viral antigen may be a full-length antigenic viral protein or a portion of the antigenic viral protein that contains the predominant antigen, neutralizing antigen, or epitope of the pathogenic virus. Alternatively, the viral antigen contains the conserved region of glycoproteins between at least two strains of the same pathogenic virus.

In a variation, the viral antigen may be a modified antigen that is mutated from a glycoprotein of the pathogenic virus such that the viral antigen is rendered non-functional as a viral component but retains its antigenicity. Such modification of the viral antigen includes deletions in the proteolytic cleavage site of the glycoprotein, and duplications and rearrangement of immunosuppressive peptide regions of the glycoprotein.

In one embodiment, a recombinant virus is provided for eliciting an immune response against multiple antigens in a host infected by the virus. The recombinant virus comprises: a plurality of antigen sequences heterologous to the recombinant virus, each encoding a viral antigen from a pathogenic virus, expression of the plurality of the antigen sequences eliciting an immune response directed against the viral antigen and cells expressing the viral antigen in the host upon infection of the host by the recombinant virus. The recombinant virus is replication competent or replication defective (i.e., incompetent).

According to the embodiment, the recombinant virus may be constructed from any virus, where the native progenitor is replication competent or is rendered replication defective. For example, adenovirus, adeno-associated virus (AAV), SV40 virus, retrovirus, herpes simplex virus or vaccinia virus may be used to generate the recombinant virus by inserting the viral antigen into the region non-essential to the infectivity of the recombinant virus. It is preferred that the recombinant virus does not have the pathologic regions of the native progenitor of the wild type virus but retains its infectivity to the host.

Also according to the embodiment, the plurality of the antigen sequences may be multiple copies of the same antigen sequence or multiple antigen sequences that differ from each another.

In a variation of the embodiment, at least two of the plurality of the antigen sequences are expressed from a promoter bicistronically via an internal ribosomal entry site or via a splicing donor-acceptor mechanism.

Alternatively, at least two of the plurality of the antigen sequences are expressed from a promoter to form a fusion protein.

Also according to the embodiment, the expression of the viral antigen may be controlled by a promoter homologous to the native progenitor of the recombinant virus. Alternatively, the expression of the viral antigen may be controlled by a promoter heterologous to the native progenitor of the recombinant virus. For example, the promoter heterologous to the native progenitor of the recombinant virus may be a eukaryotic promoter such as insulin promoter, human cytomegalovirus (CMV) promoter and its early promoter, simian virus SV40 promoter, Rous sarcoma virus LTR promoter/enhancer, the chicken cytoplasmic β-actin promoter, and inducible promoters such as the tetracycline-inducible promoter.

Also according to the embodiment, the plurality of antigen sequences may be a combination of antigens from at least two strains of the same pathogenic virus.

Optionally, the plurality of antigen sequences may be a combination of antigens from at least two different pathogenic viruses. For example, the plurality of antigen sequences may be a combination of antigens from HIV-1, HIV-2, herpes simplex virus type 1, herpes simplex virus type 2, influenza virus, Marburg virus, Ebola virus, and hepatitis A, B, C, D, and E viruses.

The DNA sequence encoding viral antigen(s) is inserted into any non-essential region of the wild type virus. In the case of adenovirus, for example, the nucleic acid is preferably inserted into the E1, E3 and/or E4 region of the adenovirus. Because the E1, E3 and E4 regions are available as insertion sites, the present invention also contemplates separate insertion of more than one encoding sequence.

In the recombinant viral vector vaccines of the present invention, the selected nucleotide sequences of the viral antigens are operably linked to control elements that direct transcription or expression thereof in the subject in vivo. Either homologous or heterologous viral control sequences can be employed. Useful heterologous control sequences generally include those derived from sequences encoding host or viral genes. Examples include, but are not limited to a cytomegalovirus (CMV) promoter such as the CMV immediate early promoter region ($CMV_{ie}$), SV40 early promoter, mouse mammary tumor virus LTR promoter, adenovirus major late promoter (AdMLP), a herpes simplex virus promoter, and a retrovirus LTR promoter. Preferably, any strong constitutive promoter may be operatively linked to nucleotide sequences of the viral antigens. More preferably the viral promoter is CMV immediate early promoter ($CMV_{ie}$).

The present invention also relates to a pharmaceutical composition comprising the vaccine(s) described above, and a pharmaceutically acceptable diluent, carrier, or excipient carrier. Additionally the vaccine may also contain an aqueous medium or a water containing suspension, often mixed with other constituents in order to increase the activity and/or the shelf life. These constituents may be salt, pH buffers, stabilizers (such as skimmed milk or casein hydrolysate), emulsifiers, and preservatives.

An adjuvant may be included in the pharmaceutical composition to augment the immune response to the viral antigen expressed from the recombinant virus. Examples of the adjuvant include, but are not limited to, muramyl dipeptide, aluminum hydroxide, saponin, polyanions, amphipatic substances, bacillus Calmette-Guerin (BCG), endotoxin lipopolysaccharides, keyhole limpet hemocyanin (KLH), interleukin-2 (IL-2), and granulocyte-macrophage colony-stimulating factor (GM-CSF).

The present invention also provides kits for enhancing the immunity of a host to a pathogen. These kits may include any one ore more vaccines according to the present invention in combination with a composition for delivering the vaccine to a host and/or a device, such as a syringe, for delivering the vaccine to a host.

The vaccine according to the invention is administered as a pre-exposure (or post-exposure) single dose in a manner compatible with the dosage formulation, and in such amount as will be prophylactively effective, i.e., the amount of immunizing antigen or recombinant microorganism capable of expressing the antigen that will induce immunity in humans or other hosts against challenge by the pathogenic virus, such as virulent Ebola virus, HIV, and hepatitis A, B, C, D, and E virus. Immunity is defined as the induction of a significant level of protection after vaccination compared to an unvaccinated human or other host.

The vaccine of the present invention, i.e., the recombinant virus, may be administered to a host, preferably a human subject, via any pharmaceutically acceptable routes of administration. The routes of administration include, but are not limited to, intramuscular, intratracheal, subcutaneous, intranasal, intradermal, rectal, oral and parental route of administration. Routes of administration may be combined, if desired, or adjusted depending upon the type of the pathogenic virus to be immunized against and the desired body site of protection.

Doses or effective amounts of the recombinant virus may depend on factors such as the condition, the selected viral antigen, the age, weight and health of the host, and may vary among hosts. The appropriate titer of the recombinant virus of the present invention to be administered to an individual is the titer that can modulate an immune response against the viral antigen and elicits antibodies against the pathogenic virus from which the antigen is derived. An effective titer can be determined using an assay for determining the activity of immunoeffector cells following administration of the vaccine to the individual or by monitoring the effectiveness of the therapy using well known in vivo diagnostic assays. For example, a prophylactically effective amount or dose of a recombinant adenovirus of the present invention may be in the range of from about 100 µl to about 10 ml of saline solution containing concentrations of from about $1 \times 10^4$ to $1 \times 10^8$ plaque forming units (pfu) virus/ml.

Practicing the present invention employs, unless otherwise indicated, conventional methods of virology, microbiology, molecular biology and recombinant DNA techniques within the skill of the art. Such techniques are explained fully in the literature. See, e.g., Sambrook, et al. Molecular Cloning: A laboratory Manual; DNA Cloning: A Practical Approach, vol I & II (D. Glover ed.); Oligonucleotide Synthesis (N. Giat, ed.); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.).

Ebola Virus Disease Progression

Typically, Ebola virus infection runs its course within 14 to 21 days. Infection initially presents with nonspecific flu-like symptoms such as fever, myalgia, and malaise. As the infection progresses, patients exhibit severe bleeding and coagulation abnormalities, including gastrointestinal bleeding, rash, and a range of hematological irregularities, such as lymphopenia and neutrophilia. Cytokines are released when reticuloendothelial cells encounter virus, which can contribute to exaggerated inflammatory responses that are not protective. Damage to the liver, combined with massive viremia, leads to disseminated intravascular coagulopathy. The virus eventually infects microvascular endothelial cells and compromises vascular integrity. The terminal stages of Ebola virus infection usually include diffuse bleeding, and hypotensive shock accounts for many Ebola virus fatalities (Colebunders, R. and M. Borchert 2000 *J Infect* 40:16-20; Sanchez, A. et al. 2001 Filoviridae: Marburg and Ebola viruses in Fields Virology, D. M. Knipe and P. M. Howley (eds.), Lippincott, Williams & Wilkins, Philadelphia, Pa. p. 1279-1304).

Structure and Classification of the Ebola Virus

Ebola virus and the related Marburg virus are members of the Filovirus family, which are pleomorphic, negative-sense RNA viruses whose genome organization is most similar to the Paramyxoviridae. Of the four identified strains of Ebola virus, three (the Zaire, Ivory Coast, and Sudan strains) have been shown to cause disease in both humans and nonhuman primates, with the Zaire strain exhibiting the highest lethality rate (Feldmann, H. et al. 1994 *Virology* 199:469-473; Sanchez, A. et al. 1996 *PNAS USA* 93:3602-3607). The only documented outbreaks of Ebola virus infection in the United States were fortunately restricted to nonhuman primates at holding facilities in Virginia and Texas, caused by the Reston strain, which has not yet caused fatal disease in humans (Jahrling, P. B. et al. 1990 *Lancet* 335:502-505).

The Ebola virus genome is 19 kb long, with seven open reading frames encoding structural proteins, including the virion envelope glycoprotein (GP), nucleoprotein (NP), and matrix proteins VP24 and VP40; nonstructural proteins, including VP30 and VP35; and the viral polymerase (Sanchez, A. et al. 2001 Filoviridae: Marburg and Ebola viruses in Fields Virology, D. M. Knipe and P. M. Howley (eds.), Lippincott, Williams & Wilkins, Philadelphia, Pa. p. 1279-1304). Unlike that of Marburg virus, the GP open reading frame of Ebola virus gives rise to two gene products, a soluble 60- to 70-kDa protein (sGP) and a full-length 150- to 170-kDa protein (GP) that inserts into the viral membrane (Sanchez, A. et al. 1996 *PNAS USA* 93:3602-3607; Volchkov, V. E. et al. 1995 *Virology* 214:421-430), through transcriptional editing.

Ebola Virus GP and Viral Pathogenesis

The Ebola virus GP is synthesized in a secreted (sGP) or full-length transmembrane form, and each gene product has distinct biochemical and biological properties. For example, GP appears to form a trimeric complex (Sanchez, A. et al. 1998 *J Virol* 72:6442-6447) and binds preferentially to endothelial cells, whereas sGP does not (Yang, Z.-Y. et al. 1998 *Science* 279:1034-1037). In contrast to GP, sGP gives rise to a dimeric protein (Sanchez, A. et al. 1998 *J Virol* 72:6442-6447) that interacts with neutrophils (Yang, Z.-Y. et al. 1998 *Science* 279:1034-1037).

Several lines of evidence suggest that the viral GP plays a key role in the manifestations of Ebola virus infection. The transmembrane form of GP targets the Ebola virus to cells that are relevant to its pathogenesis. Specifically, GP allows the virus to introduce its contents into monocytes and/or macrophages, where cell damage or exposure to viral particles may cause the release of cytokines (Ströher, U. et al. 2001 *J Virol* 75:11025-11033) associated with inflammation and fever, and into endothelial cells, which damages vascular integrity (Yang, Z.-Y. et al. 2000 *Nat Med* 6:886-889). Thus, sGP may alter the immune response by inhibiting neutrophil activation, while the transmembrane GP may contribute to the hemorrhagic fever symptoms by targeting virus to cells of the reticuloendothelial network and the lining of blood vessels.

Structural analyses of GP have revealed features in common with other viral envelope proteins. The crystal structure of the GP ectodomain revealed a coiled-coil domain resembling a trimer of helical hairpin-like loops (Malashkevich, V. N. et al. 1999 *PNAS USA* 96:2662-2667; Weissenhorn, W. et al. 1998 *Mol Cell* 2:605-616). The hairpin structure is adjacent to the fusion-peptide region (Ito, H. et al., 1999 *J Virol* 73:8907-8912) hypothesized to insert directly into the target cell membrane. Analogous coiled-coil regions have been defined for GPs of influenza virus, murine retroviruses, HIV, and simian immunodeficiency virus (SIV) as well as for some cellular proteins, called SNARES, that function in intracellular vesicle fusion (Weissenhorn, W. et al. 1998 *Mol Cell* 2:605-616). For HIV gp160, it has been possible to identify peptides that bind to a transient intermediate form that precedes hairpin formation. Because of their potent inhibition of viral entry, these reagents have shown considerable promise in clinical trials (Kilby, J. M. et al. 1998 *Nat Med* 4:1302-1307). The Ebola virus GP contains a homologous hairpin structure for which a possible inhibitory peptide has been identified (Watanabe, S. 2000 *J Virol* 74:10194-10201), a region that remains a therapeutic target.

Accelerated Vaccination for Ebola Virus Haemorrhagic Fever in Non-Human Primates Mice were immunized with plasmid DNA encoding Ebola GP, the trimeric virion-associated glycoprotein (Sanchez, A. et al. 1998 *J Virol* 72:6442-6447) involved in cellular pathogenicity (Yang, Z.-Y. et al. 2000 *Nature Med* 6:886-889; Volchkov, V. E. et al. 2001 *Science* 291:1965-1969; Chan, S. Y. et al. 2000 *J Gen Virol* 81:2155-2159; Takada, A. et al. 2000 *Virology* 278:20-26), followed by boosting with ADV-GP, or with ADV-GP only. The antibody response, a surrogate for protection (Sullivan, N. J. et al. 2000 *Nature* 408:605-609; Xu, L. et al. 1998 *Nature Med* 4:37-42), was measured using an enzyme-linked immunosorbent assay (ELISA). After DNA vaccination, titers were modest but increased 100- to 1,000-fold with ADV-GP boosting (FIG. 1a). In contrast, vaccination with ADV-GP gave rise to a lower antibody titer, but it was generated more rapidly. To investigate whether immunization with adenoviral vectors alone might protect against Ebola virus infection, alternative immunization schedules in macaques were developed for comparison to the previous DNA/ADV protocol (FIG. 1b, middle and bottom panels compared with top panel).

Figure 1B:
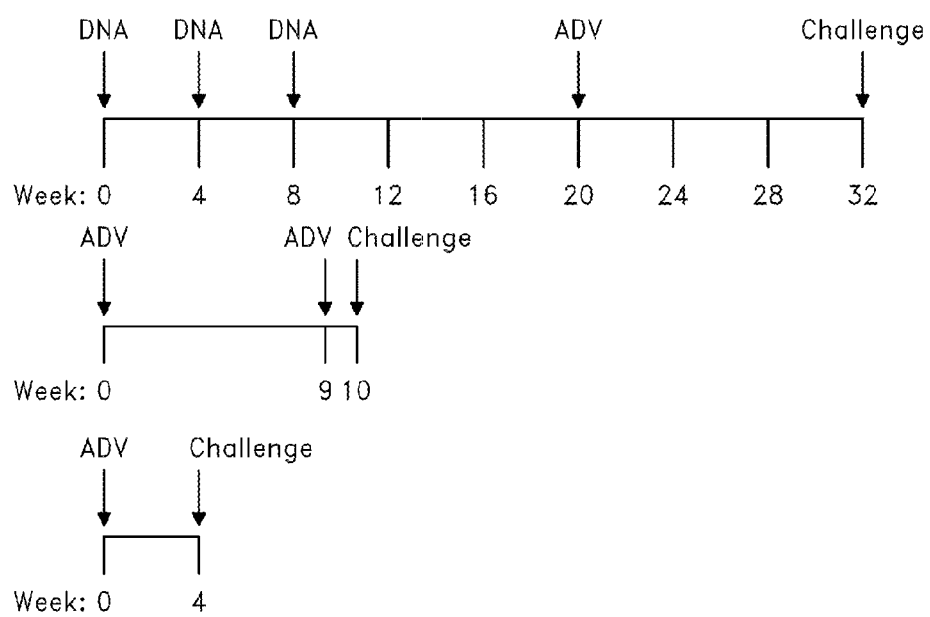
Figure 2:
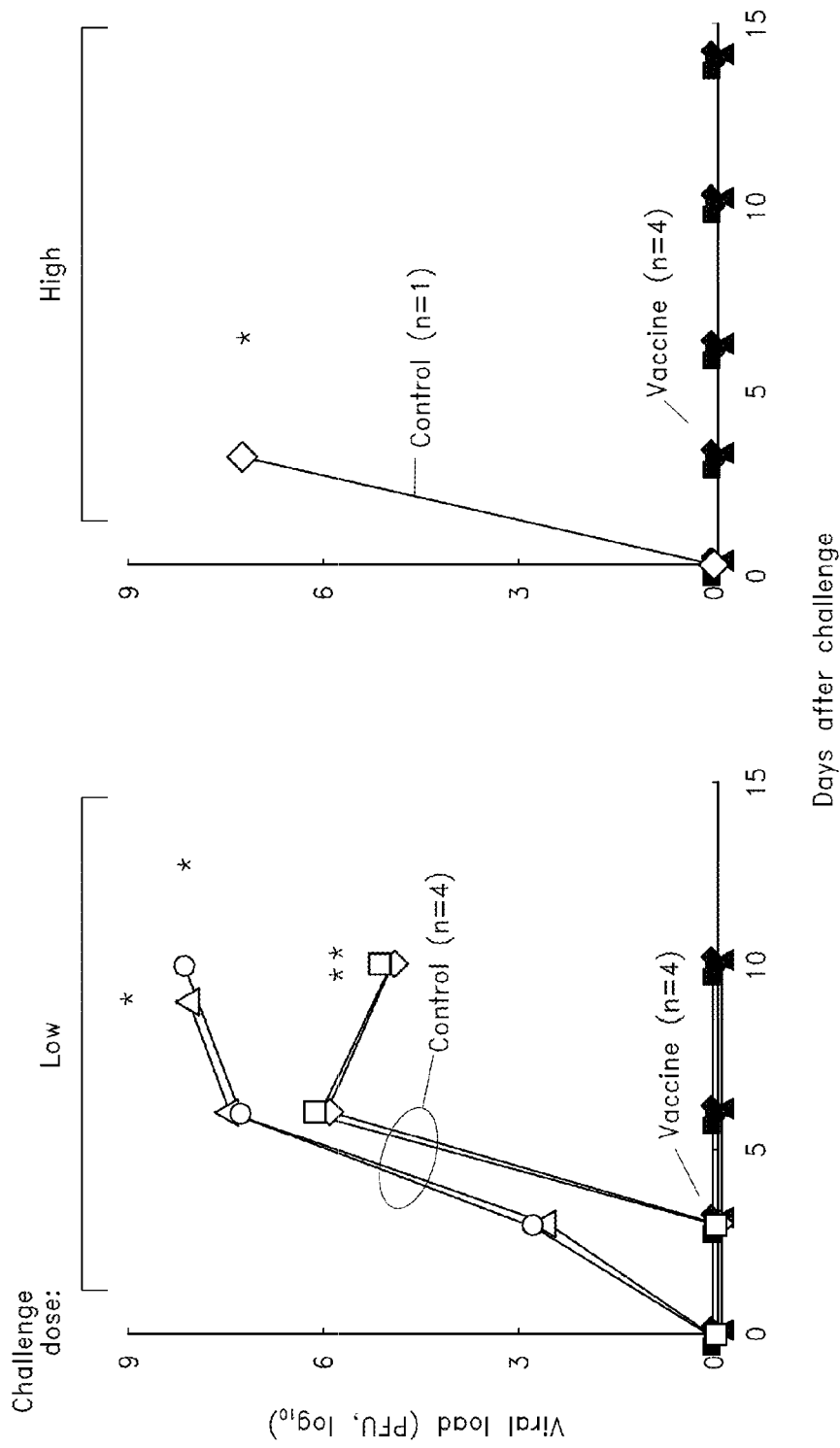
FIG. 2. Protection against lethal challenge in non-human primates using adenoviral priming and boosting. Plasma viraemia in monkeys after infection with Ebola virus. Asterisks represent the time of death in control animals. The data represent the reciprocal endpoint dilution of serum for each monkey. Results are shown for four immunized animals challenged with Ebola Zaire at 13 PFUs (low dose; filled symbols, left), four immunized animals challenged at 1,500 PFUs (high dose; filled symbols, right), and five saline-injected control animals (open symbols).
Figure 3A:
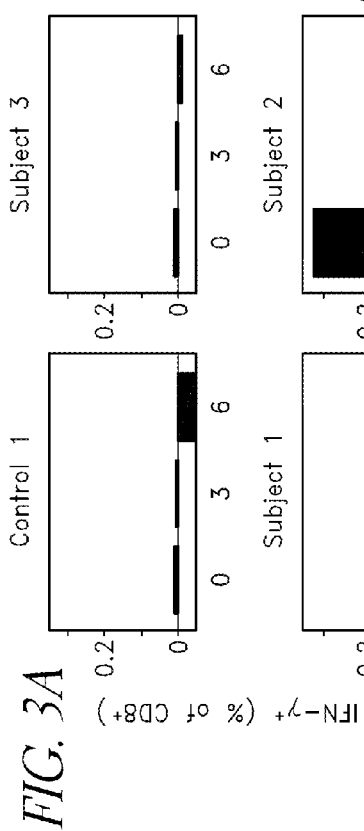
FIG. 3. Immune responses to adenoviral prime and boost vaccination in cynomolgus macaques. a) Intracellular flow cytometry was performed to quantify IFN-γ production from Ebola-specific CD8 lymphocytes from saline injected (control) or ADV-GP/NP immunized (subject) monkeys at weeks 0 and 9. Immune responses before (day 0) and after (days 3, 6) challenge at week 10 are shown for CD8 cells. No substantial increases were observed in the CD4 population. Non-stimulated cells gave responses similar to those of the control subjects, at background levels. The gating strategy used for flow cytometric data was as follows: Lymphocytes were selected using a forward vs. side scatter gate. CD8 cells were defined by first gating on the CD3+/CD4− population, followed by selection for CD8+ stained cells. The CD8 gate was lowered to include cells that had down-regulated CD8 due to activation. CD4 cells were defined by first gating on the CD3+/CD8− population, followed by selection of CD4+ stained cells. Cytokine positive cells were defined as a percentage of the subset. b) ELISA titers of Ebola-specific antibodies in serum of vaccinated animals collected at week 0 (pre-immune, left), week 9 (pre-boost, middle) and week 10 (day of challenge, right) relative to the time of the first immunization. ELISA results represent endpoint dilution titers determined by optical density as described in Example 1.
Figure 3B:
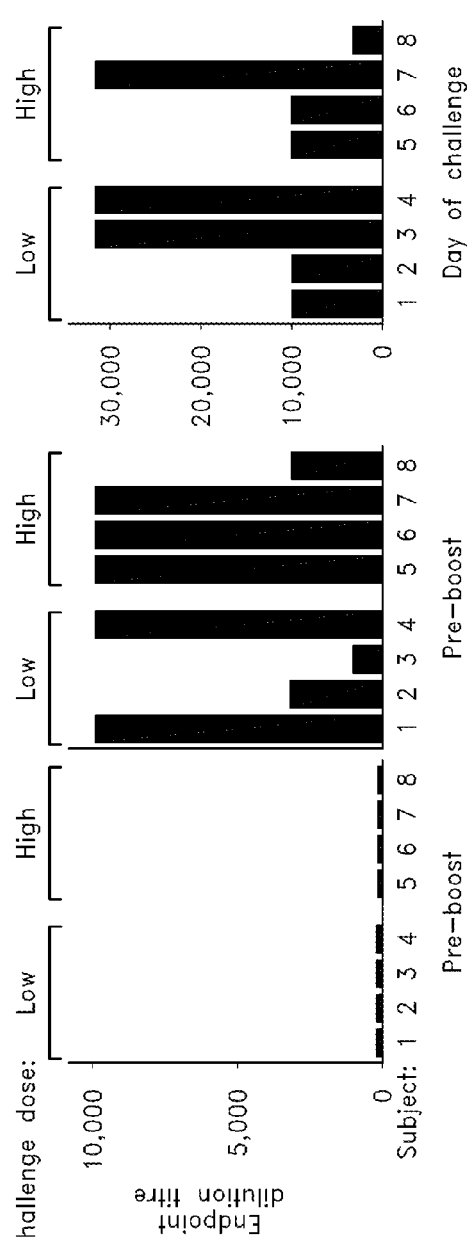

Cynomolgus macaques were immunized with ADV-GP and ADV-NP, followed by boosting 9 weeks later (FIG. 1b, middle panel). One week after the boost, animals were challenged with either a low (13 plaque-forming units (PFUs)) or high (1,500 PFUs) dose of a 1995 isolate of Ebola virus Zaire. These doses were uniformly fatal 6-12 days afterwards in saline-injected control animals. In contrast, the ADV-GP/NP immunized monkeys (n=4) were completely protected, confirmed by viral load (FIG. 2). Analysis of the cell-mediated and humoral immune responses revealed significant increases in the CD8+ T-cell response to Ebola antigens by intracellular cytokine staining for interferon (IFN)-γ, seen before exposure to virus, in contrast to control animals where no response was seen (FIG. 3a). Similarly, antibody titers to the virus were stimulated in vaccinated animals, which minimally increased after the viral challenge (FIG. 3b). No substantial increases were observed in the numbers of Ebola-specific CD4+ T cells at this time. Both CD8+ cellular and humoral immune responses therefore were associated with protection.

Figure 4B:
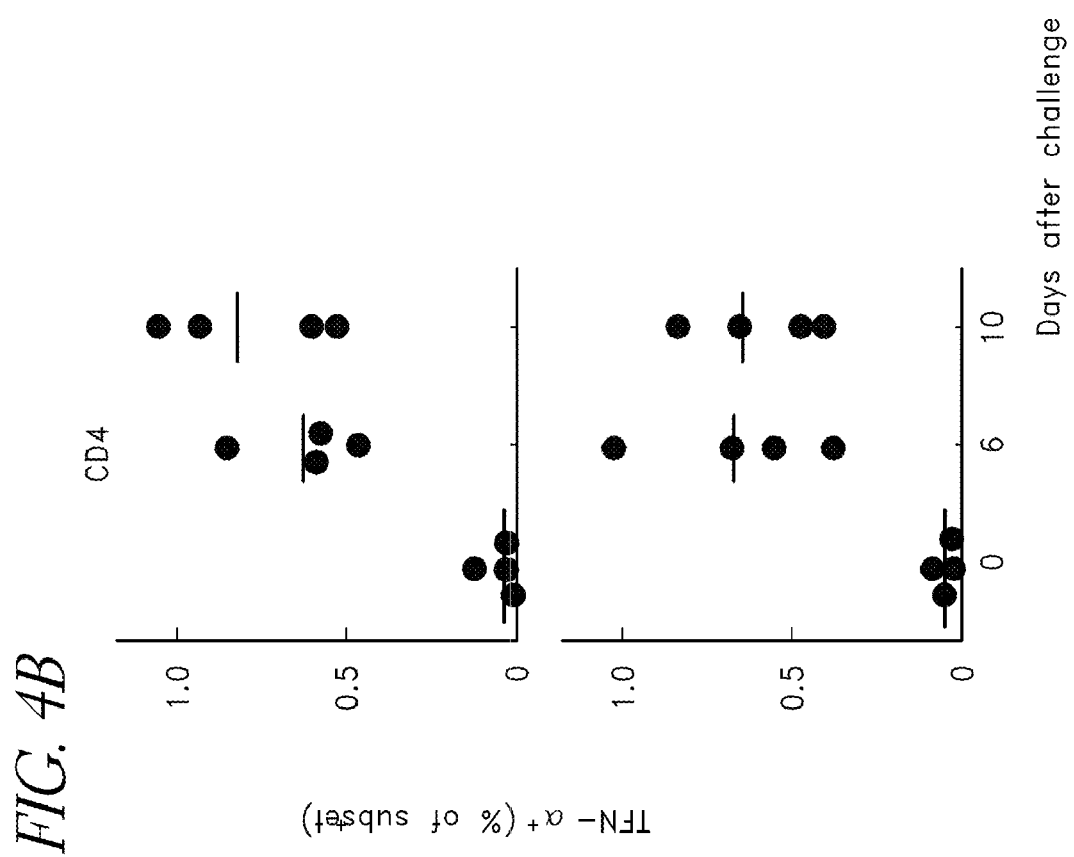
FIG. 4. Protection against lethal challenge in non-human primates using a single adenoviral immunization. a) Immunization and challenge were performed with the 1995 Zaire subtype Ebola virus as in FIG. 1b (bottom), and plasma viraemia in monkeys after challenge was measured as above (see FIG. 2) for four immunized animals inoculated with 18 PFUs (low dose; filled symbols, left) and four animals injected with 1,762 PFUs (high dose; filled symbols, right) or two saline-injected controls (open symbols). b) Intracellular flow cytometry was performed using antibodies to TNF-α in CD4 and CD8 lymphocytes from immunized monkeys (subject), each panel representing an individual macaque. Immune responses before (day 0) and after (days 6, 10) challenge on day 28 are shown. Horizontal bars indicate the average value per group, and filled circles represent values for individual subjects. c) Endpoint dilution ELISA titers of Ebola-specific antibodies in serum collected two weeks after immunization with ADV-GP/NP, determined by optical density as described in Example 1. d) Kaplan-Meier survival curve of macaques, immunized as indicated, and challenged with a low or high dose of PFUs of Ebola virus.
Figure 4C:
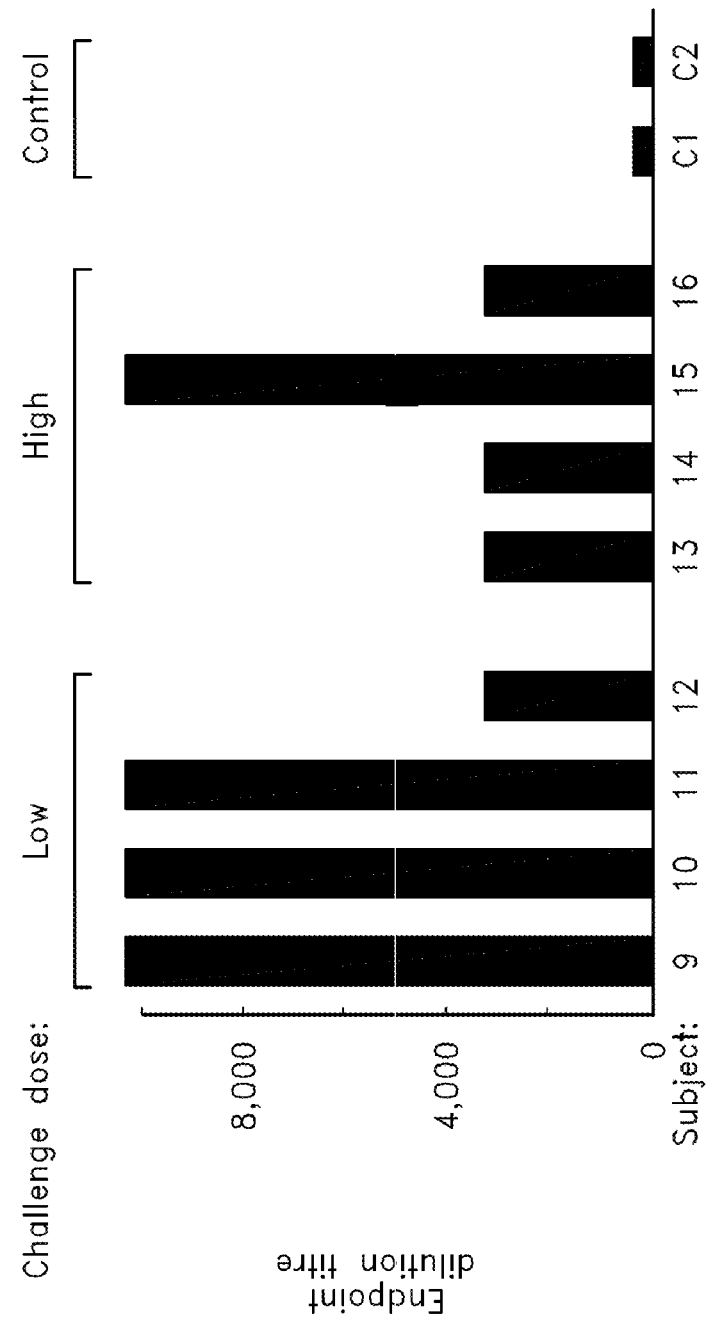
Figure 4D:
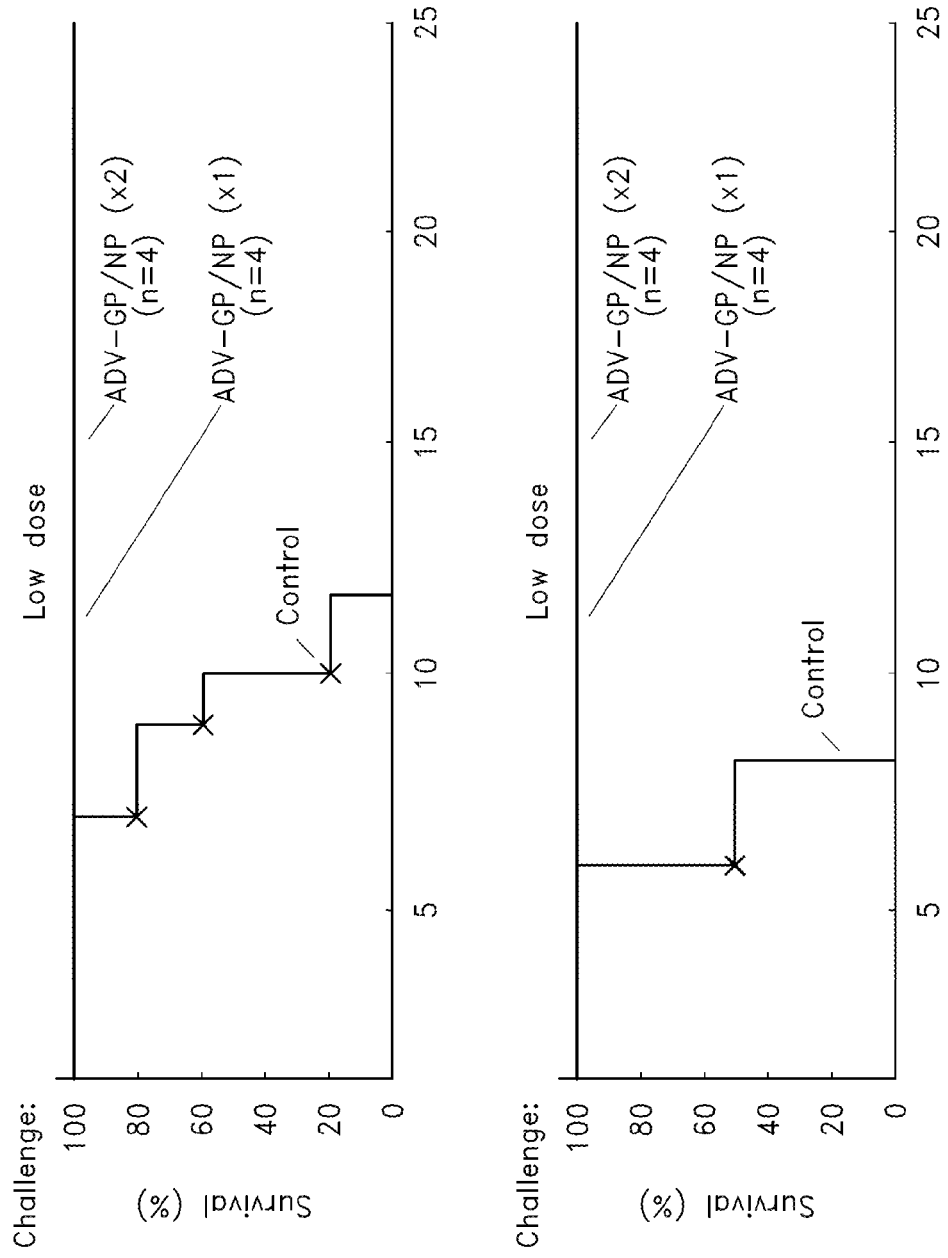

A second adenoviral immunization did not substantially increase the Ebola-specific immune responses, raising the notion that the primary immunization was sufficient to confer protection. To address this possibility, a single immunization was given, and animals were challenged one month afterwards (FIG. 1b, bottom panel). Both at low and high viral challenge doses, animals were completely protected against infection (FIG. 4a). In this case, changes in the intracellular IFN-γ response in T lymphocytes were not consistently seen; however, Ebola-specific T-cell responses were detected with intracellular tumor-necrosis factor (TNF)-α. CD8 responses were observed before challenge or were induced soon thereafter in five of eight animals, once again correlating with protection against infection (FIG. 4b, right). In contrast, CD4+ responses, not detectable before inoculation, increased after challenge (FIG. 4b, left). Immunoglobulin-γ (IgG) antibody titers, readily detected at the time of inoculation, were also associated with protection (FIG. 4c). These data demonstrated that a single ADV-GP/NP injection can accelerate vaccine protection and long-term survival against Ebola in non-human primates (FIG. 4d).

Ebola virus infection is characterized by its rapid onset, high person-to-person transmissibility, and significant mortality rate. The mainstay of treatment has been supportive therapy, and prevention has been dependent on containment using barrier precautions. Effective protection was achieved previously in primates with a heterologous DNA prime and adenoviral boost strategy. The prime-boost immunization relies on the ability of the adenoviral boost to expand the primary T-cell response induced by DNA vaccination. When animals are primed with ADV vectors alone, a robust Ebola-virus-specific cellular and humoral immune response is more rapidly achieved, although the response to a second ADV-GP/NP injection is blunted, probably because of anti-vector immunity. Here, we explored the possibility that this more rapid initial immune response may nonetheless confer protection and outweigh the stronger immune response that requires additional time. A single immunization with an adenoviral vector encoding Ebola virus proteins is sufficient to confer protection against lethal challenge within four weeks, and this response correlates with both cellular and humoral immune responses to the infection.

Although antibody titers correlated here with the protective response, previous studies in non-human primates have suggested that the passive transfer of antibody is insufficient to provide long-lasting protection against Ebola virus (Jahrling, P. B. et al. 1999 *J Infect Dis* 179:S224-S234). In rodent studies with adapted Ebola virus, passive transfer of antibodies (Parren, P. W. et al. 2002 *J Virol* 76:6408-6412; Gupta, M. et al. 2001 *J Virol* 75:4649-4654) or adoptive transfer of cytotoxic T cells (Wilson, J. A. & Hart, M. K. 2001 *J Virol* 75:2660-2664) showed protection when given before infection. A more sensitive but less quantitative CD4 lymphoproliferative response correlated with protection in the previous DNA/ADV prime-boost study, in which CD8 responses were not measured (Sullivan, N. J. et al. 2000 *Nature* 408: 605-609). In addition to the antibody response induced by the vaccine in the present study, both CD4 and CD8 responses were observed after the challenge. The fact that CD4 responses were not observed before challenge in either protocol whereas CD8 responses were more consistently seen beforehand suggests that the CD8 response is likely to have an important role in protection in non-human primates, but further analysis will be required to assess the relative importance of the cellular and humoral immune responses in the mechanism of protection.

The approach to single vaccine injection with ADV vectors is relevant to the containment and treatment of Ebola virus and related outbreaks that are continuing to emerge in central Africa. This vaccine approach is envisioned as proving effective in humans, and we envision ring vaccination as being used to contain outbreaks, similar to smallpox in the past. This result also suggests alternative strategies for vaccination against Ebola or other acute pathogenic diseases. The prime-boost strategy remains more immunologically potent and, if the response is highly durable, may still be useful for preventative vaccines, for example, in hospital workers. In contrast, the single adenoviral vaccine administration may be better used during acute outbreaks. It is also possible that alternative viral vectors, such as those derived from other adenovirus serotypes or from poxvirus vectors, might be used to boost an ADV type 5 vector primary immunization. Alternative ADV serotypes will also help to overcome immunity to natural ADV type 5 infection that could potentially reduce vaccine efficacy in some populations. A one-shot vaccine is envisioned as being helpful in the control of Ebola virus outbreaks in great ape populations of central Africa (Walsh, P. D. et al. 2003 Nature 422:611-614). Analogous single dose ADV vector immunization is envisioned as being used for other emerging and highly lethal infectious pathogens, such as Marburg, Lassa or the SARS coronavirus.

EXAMPLE 1

Vector Construction

ADV-GP and ADV-NP were prepared as described previously (Sullivan, N. J. et al. 2000 Nature 408:605-609). The recombinant adenoviral vector was made according to previously published methods (Aoki, K. et al. 1999 Mol Med 5:224-231). A dose of $10^{10}$ (mice) or $10^{12}$ (non-human primates) adenoviral vector particles for each component was administered to each animal without adverse effects.

Animal Study and Safety

Twenty cynomolgus macaques (*Macaca fascicularis*), 3 yr old and weighing 2-3 kg, obtained from Covance, were used for immunization and challenge experiments. The monkeys, housed singly, were anaesthetized with ketamine to obtain blood specimens and to administer vaccines. They received regular enrichment according to the Guide for the Care and Use of Laboratory Animals (DHEW number NIH 86-23). Before Ebola virus challenge and to the end of each experiment, the animals were maintained in the Maximum Containment Laboratory (BSL-4) and fed and checked daily.

Mouse Immunization

DNA and adenoviral vectors expressing Ebola Zaire glycoprotein (Mayinga strain) were constructed as described previously (Xu, L. et al. 1998 Nature Med 4:37-42; Ohno, T. et al. 1994 Science 265:781-784) with gene expression under control of the cytomegalovirus enhancer and promoter in the plasmid. Mice (n=10 per group) were immunized intramuscularly with 100 μg DNA (pGP) and/or $10^{10}$ particles of adenovirus (ADV-GP). DNA vaccination was performed on days 0, 14 and 24 with adenoviral boost on day 42. Adenoviral injection was performed on days 0 and 42, and samples were collected for ELISA titers at the indicated times. ELISA IgG titers were determined using 96-well plates as previously described (Ksiazek, T. G. et al. 1992 *J Clin Microbiol* 30:947-950), and specific antigen binding was detected using a goat anti-human IgG (H+L)-horseradish conjugate and ABTS/peroxide (substrate/indicator).

ELISA

Polyvinyl chloride ELISA plates (Dynatech) were coated with 50 μl antigen per well and incubated overnight at 4° C. All further incubations were carried out at room temperature. The antigen used was purified Ebola virus (about 1 mg ml$^{-1}$ total protein) inactivated by gamma irradiation. Plates were then washed five times with PBS containing Tween-20. Test sera were diluted in half-log concentrations from 1:31.6 through to 1:100,000 and allowed to react with the antigen-coated wells for 60 min. After washing plates five times, goat anti-monkey IgG (whole molecule; ICN Biomedicals) conjugated to horseradish peroxidase was used as a detection antibody. Bound IgG was detected by 2,2'-azinobis-[3-ethyl-benzothizoline-6-sulphonic acid] diammonium salt and the optical density was determined. A panel of normal serum was run each time the assay was performed. A cut-off value for a positive result was calculated as the mean optical density (at a 1:100 dilution) for the normal sera plus 3 standard deviations.

Intracellular Cytokine Analysis

Peripheral blood mononuclear cells were isolated from cynomolgus macaque whole-blood samples by separation over Ficoll. Approximately $1 \times 10^6$ cells were stimulated in 200 μl RPMI medium (GIBCO) for 6 h at 37° C. with anti-CD28 and anti-CD49d antibodies and either DMSO or a pool of 15-nucleotide peptides spanning the Ebola GP Zaire (Mayinga strain) open reading frame. The peptides were 15 nucleotides overlapping by 11 spanning the entire Ebola glycoprotein at a final concentration of 2 μg ml$^{-1}$. Cells were fixed and permeablized with FACS lyse (Becton Dickinson) supplemented with Tween-20, and stained with a mixture of antibodies against lineage markers (CD3-PE, CD4-PerCP, CD8-FITC) and either TNF-APC or IFN-γ-APC. Samples were run on a FACS Calibur and analysed using the software FlowJo. Positive gating for lymphocytes using forward versus side scatter was followed by CD3$^+$/CD8$^-$ and CD3$^+$/CD4$^-$ gating, and specific populations were further defined by anti-CD4 and anti-CD8 positivity, respectively. Cytokine-positive cells were defined as a percentage within these individual lymphocyte subsets, and at least 200,000 events were analysed for each sample.

Macaque Immunization

In conducting this research, the investigators adhered to the Guide for the Care and Use of Laboratory Animals, prepared by the Institute of Laboratory Animal Resources, National Research Council. The facilities are fully accredited by the Association for Assessment and Accreditation of Laboratory Animal Care International. Cynomolgus macaques were injected intramuscularly at the indicated times (FIG. 1b) with an equal mixture of $2 \times 10^{12}$ particles of ADV-GP and ADV-NP. Viral challenge was performed by inoculation of animals in the left or right caudal thigh with 0.5 ml of viral stock that contained a target dose of either about 10 or about 1,000 PFUs of Ebola virus (Zaire species) at ten weeks (FIG. 2) or four weeks (FIG. 4) after the initial immunization, and actual titer was confirmed by plaquing. No adverse effects of the adenovirus vaccination were observed acutely. The Ebola virus used in this study was originally obtained from a fatally infected human from the former Zaire in 1995 (Jahrling, P. B. et al. 1996 *Arch Virol Suppl* 11:135-140). Collection of serum and blood for viral load and ELISA titers was performed as previously described (Sullivan, N. J. et al. 2000 Nature 408: 605-609).

While the present invention has been described in some detail and form for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A method of inducing a protective immune response by administering a single dose of a recombinant adenovirus to a host, said recombinant adenovirus comprising:
    an antigen sequence that encodes a full length Ebola virus glycoprotein, expression of the glycoprotein eliciting an immune response directed against the glycoprotein and cells expressing the glycoprotein in the host upon infection of the host by the recombinant adenovirus,
    wherein said single dose comprises at least $10^{10}$ recombinant adenovirus particles and is sufficient to induce a protective immune response comprising an antibody response and a CD8+ T-cell response to the glycoprotein.

2. The method of claim 1, wherein the recombinant adenovirus is a replication defective adenovirus.

3. The method of claim 2, wherein the recombinant adenovirus is adenovirus type 5.

4. The method of claim 2, wherein the antigen sequence that encodes the full length Ebola virus glycoprotein is positioned in the E1, E3 or E4 region of the adenovirus.

5. The method of claim 1, wherein the expression of the glycoprotein is controlled by a promoter homologous to a native progenitor of the recombinant adenovirus.

6. The method of claim 1, wherein the expression of the glycoprotein is controlled by a promoter heterologous to a native progenitor of the recombinant adenovirus.

7. The method of claim 6, wherein the promoter is heterologous to a native progenitor of the recombinant adenovirus and is a promoter selected from the group consisting of CMV promoter, SV40 promoter, retrovirus LTR promoter, and chicken cytoplasmic β-actin promoter.

8. A method of inducing a protective immune response by administering a single dose of a recombinant adenovirus to a host, said recombinant adenovirus comprising:
   a plurality of antigen sequences, each encoding a full length Ebola virus glycoprotein, expression of the plurality of the antigen sequences eliciting an immune response directed against the glycoprotein and cells expressing the glycoprotein in the host upon infection of the host by the recombinant adenovirus;
   wherein said single dose comprises at least $10^{10}$ recombinant adenovirus particles and is sufficient to induce a protective immune response comprising an antibody response and a CD8+ T-cell response to the glycoprotein.

9. The method of claim 1 or 8, wherein the single dose comprises about $10^{12}$ recombinant adenovirus particles.

* * * * *